United States Patent
Zhou et al.

(10) Patent No.: US 8,308,642 B2
(45) Date of Patent: Nov. 13, 2012

(54) SPECTROSCOPIC DIAGNOSTIC APPARATUS AS AN AID FOR LASER TATTOO REMOVAL

(75) Inventors: Xin Jack Zhou, Hockessin, DE (US); Sean Xiaolu Wang, Wilmington, DE (US)

(73) Assignee: BWT Property, Inc., Newark, DE (US)

( * ) Notice: Subject to any disclaimer, the term of this patent is extended or adjusted under 35 U.S.C. 154(b) by 1561 days.

(21) Appl. No.: 11/674,299

(22) Filed: Feb. 13, 2007

(65) Prior Publication Data
US 2007/0197883 A1    Aug. 23, 2007

Related U.S. Application Data

(60) Provisional application No. 60/766,901, filed on Feb. 17, 2006.

(51) Int. Cl.
*A61N 5/00* (2006.01)

(52) U.S. Cl. .......... 600/306; 606/3; 606/9; 606/12; 607/89

(58) Field of Classification Search .......... 600/306; 606/1–3, 9–13; 607/88–91, 94–95
See application file for complete search history.

(56) References Cited

U.S. PATENT DOCUMENTS

| | | | |
|---|---|---|---|
| 4,973,848 A | 11/1990 | Kolobanov et al. | |
| 5,217,455 A | 6/1993 | Tan | |
| 5,531,740 A * | 7/1996 | Black | 606/9 |
| 6,015,404 A | 1/2000 | Altshuler et al. | |

* cited by examiner

*Primary Examiner* — Michael Kahelin
*Assistant Examiner* — Michael D'Angelo
(74) *Attorney, Agent, or Firm* — Frank F. Tian

(57) ABSTRACT

A spectroscopic diagnostic apparatus is disclosed as an aid for laser tattoo removal. The apparatus performs spectroscopic analysis of the tattooed skin before or during laser treatment, which provides composition information of the tattoo pigments and photometric information of the skin for optimizing laser treatment protocols automatically or manually. It also provides a simulated treatment result for the selected laser types.

9 Claims, 1 Drawing Sheet

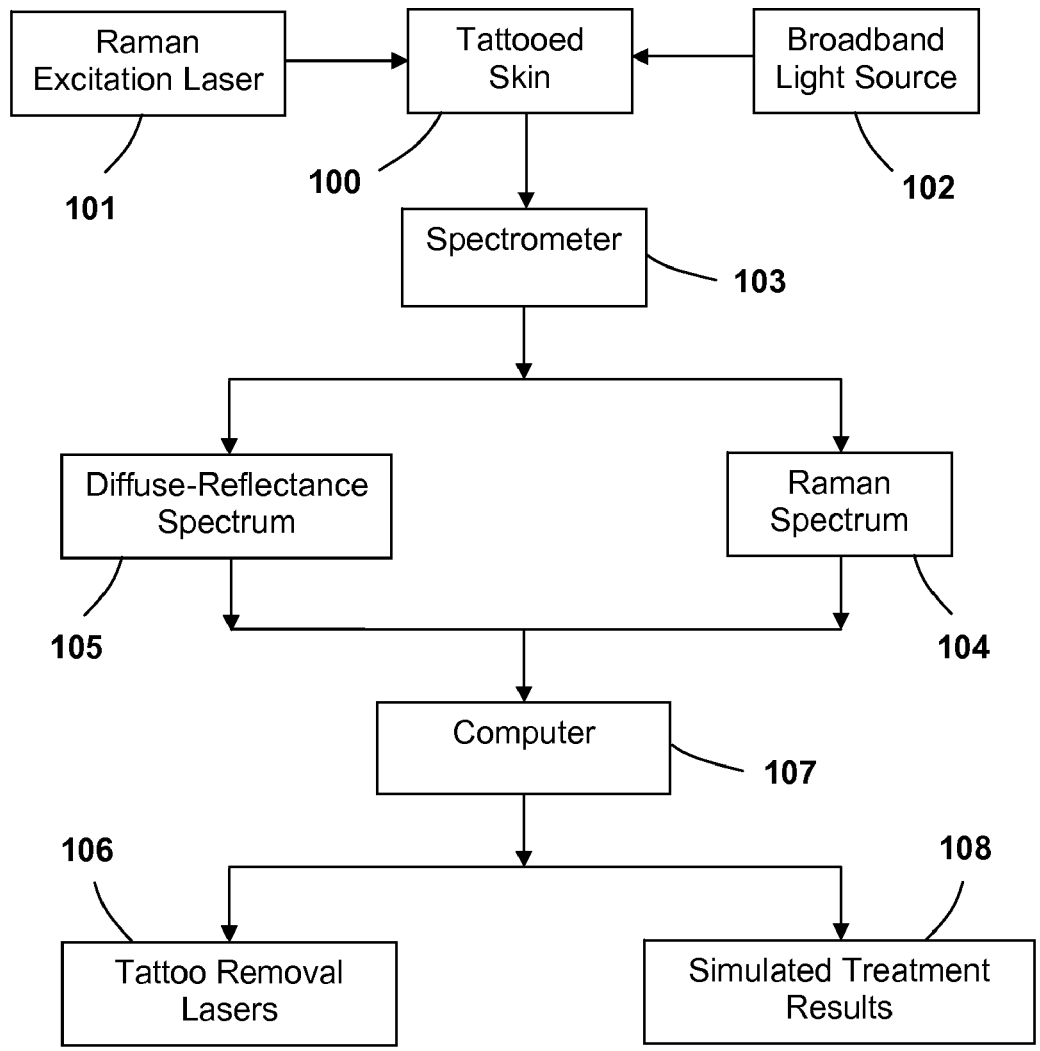

SPECTROSCOPIC DIAGNOSTIC APPARATUS AS AN AID FOR LASER TATTOO REMOVAL

REFERENCE TO RELATED APPLICATIONS

This application claims an invention which was disclosed in Provisional Patent Application No. 60/766,901, filed Feb. 17, 2006, entitled "Spectroscopic Diagnostic Apparatus as an Aid for Laser Tattoo Removal". The benefit under 35 USC § 119(e) of the above mentioned United States Provisional Applications is hereby claimed, and the aforementioned application is hereby incorporated herein by reference.

FIELD OF THE INVENTION

This invention generally relates to a diagnostic apparatus, and more specifically to a spectroscopic diagnostic apparatus for laser tattoo removal.

BACKGROUND

Tattoo (or other kinds of skin pigmentation), either artificially implanted or traumatic-inflicted, relates to pigment deposition in the inner layer of skin. Laser treatment is considered to be one of the best tattoo removal methods because it is less invasive and has a very low risk (<5%) to cause scarring. The laser treatment method generally involves the utilization of a Q-switched laser to break down the large pigment particle into small molecules with its high energy pulses, which molecules are then removed by the scavenger cells of the body. One difficulty facing laser treatment method is that the treatment result is very hard to predict, especially for those artificial tattoos, since there are over 100 tattoo pigments used in the market and the exact composition of a given tattoo pigment is often kept as a trade secret by the manufacturer. Moreover, the treatment result may be influenced by the skin type of the patient, the depth of the tattoo pigment, the size of the pigment particle, etc. On the other hand, the patients often want to 'see' the expected result before laser treatment as the whole tattoo removal procedure (generally comprising several laser treatments) is both expensive ($1,000-10,000) and time consuming (up to 2 years). There thus exists a need for a diagnostic apparatus as an aid for laser tattoo removal, which can analyze the composition of the tattoo pigments and the photometric condition of the skin. Based on the acquired information, the diagnostic apparatus should be able to provide a set of parameters for optimizing the laser treatment procedure as well as to provide a simulated laser treatment result.

SUMMARY OF THE INVENTION

According to one aspect of the present invention, a spectroscopic diagnostic apparatus is provided to measure the Raman scattering spectrum of the tattoo pigments. The composition information of the pigment is inferred from its characteristic Raman scattering peaks.

According to another aspect of the invention, the spectroscopic diagnostic apparatus is also used to measures the diffuse-reflectance spectrum of the tattooed skin. Based on the spectrum, the practitioner determines which kind of laser can be best absorbed by the tattoo pigment and what the required pulse energy is to break down the pigment particle.

According to yet another aspect of the invention, the spectroscopic diagnostic apparatus provides a simulated treatment result based on the parameters (such as wavelength, pulse energy, peak power, duty cycle, repetition rate) of the laser, the pigment composition information acquired from the Raman spectrum, and the photometric condition of the skin (which determines the absorption rate of laser energy) acquired from the diffuse-reflectance spectrum.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

FIG. 1 shows a block diagram of the spectroscopic tattoo diagnostic apparatus.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to spectroscopic diagnostic apparatus for laser tattoo removal. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

The block diagram of a preferred embodiment of the present invention is shown in FIG. 1. The spectroscopic diagnostic apparatus comprises a Raman excitation laser 101, a broadband light source 102, and one or more spectrometers 103. The Raman excitation laser 101, which can be a diode laser, a diode pumped solid state laser, or even one of the tattoo removal lasers 106 operating at low output powers, is used to excite Raman scattering from the tattooed skin 100. The Raman signal is then captured by the spectrometer 103 for spectrum analysis. Since the Raman scattering spectrum 104 of the tattoo pigment is determined by the vibration and/or rotational energy of it molecules, the composition information of the tattoo pigment can be inferred from its characteristic Raman scattering peaks. The broadband light source 102, which can be a lamp, or a light emitting diode, is used to measure the diffuse-reflectance spectrum of the tattooed skin. This spectrum is determined by the photometric condition of the tattooed skin, which is influenced by the color and particle size of the tattoo pigment, the skin type of the patient, the depth of the tattoo pigment, etc. The obtained diffuse-reflectance spectrum 105 is utilized to estimate the absorption rate for a tattoo removal laser with certain emission wavelength. Both of the two spectroscopic analysis can be performed in visible and/or near infrared (NIR) wavelengths. The spectrometer 103 employed in the present diagnostic apparatus is preferably an array spectrometer featuring high sensitivity and fast response time. But other types of spectrometers can be used as well. The Raman spectrum and diffuse-reflectance spectrum may be measured with the same spectrometer 103 or using two individual spectrometers.

The Raman spectrum 104 and diffuse-reflectance spectrum 105 of the tattooed skin 100 is sent to a computer 107 for further analysis. The composition information of the tattoo pigment is inferred from the Raman spectrum 104, whereas the absorption rate for a selected type of tattoo removal laser is calculated from the diffuse-reflectance spectrum 105. An established database of the Raman spectra for all possible tattoo pigments may help to facilitate the identification process. Based on the obtained pigment composition and absorption rate information, the computer 107 can either automatically select the appropriate parameters (such as wavelength, pulse energy, peak power, duty cycle, repetition rate) for the tattoo removal laser 106, or it can provide suggestions to the practitioner for optimizing the laser manually. The tattoo removal laser 106 preferably comprises one or more Q-switched lasers. But other types of lasers can be used as well. In addition, the computer 107 can provide a simulated treatment result 108, which is calculated based on the measured composition information of the tattoo pigment, the photometric condition of the skin, and the parameters of the selected tattoo removal lasers. The simulation result can either be a short-term result obtained after one laser treatment, or it can be a long-term result obtained after several laser treatments with different laser wavelengths and dosages.

The disclosed spectroscopic diagnostic apparatus can be directly integrated into the laser tattoo removal system or it can be used as a stand-alone device.

In the foregoing specification, specific embodiments of the present invention have been described. However, one of ordinary skill in the art appreciates that various modifications and changes can be made without departing from the scope of the present invention as set forth in the claims below. For example, other spectroscopic analysis techniques, such as fluorescence spectroscopy, can be also used in stead of or in addition to Raman spectroscopy and diffuse-reflectance spectroscopy. The diagnostic apparatus can be used to analyze any kind of skin pigmentation, either artificially induced or naturally developed. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A spectroscopic diagnostic apparatus as an aid for laser based skin pigmentation removal procedure, the spectroscopic diagnostic apparatus, either used as a stand-alone device or integrated into a laser based skin pigmentation removal system, comprising:
    a spectroscopic analyzer to perform spectroscopic analysis and generate spectroscopic data of the pigmented skin;
    non-transitory computer readable medium that when executed by a processor causes the processor to identify a composition of the pigments and estimate an absorption rate of the pigmented skin for different laser wavelengths based on the spectroscopic data acquired by the spectroscopic analyzer, and to provide a set of parameters for optimizing the laser based skin pigmentation removal procedure as well as to provide a simulated laser treatment result.

2. The spectroscopic diagnostic apparatus of claim 1, wherein the non-transitory computer readable medium causes the processor to identify the composition of either artificially induced or naturally developed skin pigmentation.

3. The spectroscopic diagnostic apparatus of claim 1, wherein the set of parameters include but are not limited to laser wavelength, pulse energy, peak power, duty cycle, and repetition rate.

4. The spectroscopic diagnostic apparatus of claim 1, wherein the spectroscopic analyzer measures a Raman scattering spectrum of the pigmented skin.

5. The spectroscopic diagnostic apparatus of claim 4, wherein the spectroscopic analyzer utilizes a pigmentation removal laser as its Raman excitation light source.

6. The spectroscopic diagnostic apparatus of claim 1, wherein the spectroscopic analyzer measures a diffuse-reflectance spectrum of the pigmented skin.

7. The spectroscopic diagnostic apparatus of claim 1, wherein the spectroscopic analyzer measures a fluorescence spectrum of the pigmented skin.

8. The spectroscopic diagnostic apparatus of claim 1, wherein the spectroscopic analysis is performed in visible and/or near infrared wavelengths.

9. A method for controlling and optimizing laser based skin pigmentation removal procedure, the method comprising the steps of:
    performing spectroscopic analysis and generating spectroscopic data of the pigmented skin with a spectroscopic analyzer;
    identifying a composition of the pigments and estimating an absorption rate of the pigmented skin for different laser wavelengths based on the spectroscopic data acquired by the spectroscopic analyzer; and
    controlling and optimizing a set of parameters of the laser based skin pigmentation removal procedure and providing a simulated laser treatment result based on the identified composition of the pigments and the estimated absorption rate of the pigmented skin.

\* \* \* \* \*